US008002915B2

(12) United States Patent
Ganta et al.

(10) Patent No.: US 8,002,915 B2
(45) Date of Patent: Aug. 23, 2011

(54) GAS GENERANT COMPOSITIONS

(75) Inventors: Sudhakar R. Ganta, Troy, MI (US); Cory G. Miller, North Royalton, OH (US); Graylon K. Williams, Warren, MI (US)

(73) Assignee: TK Holdings, Inc., Armada, MI (US)

( * ) Notice: Subject to any disclaimer, the term of this patent is extended or adjusted under 35 U.S.C. 154(b) by 904 days.

(21) Appl. No.: 11/906,345

(22) Filed: Oct. 1, 2007

(65) Prior Publication Data
US 2009/0008002 A1 Jan. 8, 2009

Related U.S. Application Data

(60) Provisional application No. 60/848,684, filed on Sep. 30, 2006.

(51) Int. Cl.
C06B 31/00 (2006.01)
(52) U.S. Cl. ............................................. 149/45
(58) Field of Classification Search .................. None
See application file for complete search history.

(56) References Cited

U.S. PATENT DOCUMENTS

| | | | | |
|---|---|---|---|---|
| 3,719,604 | A | 3/1973 | Prior et al. | 252/186 |
| 3,954,528 | A | 5/1976 | Chang et al. | 149/19.4 |
| 4,142,029 | A | 2/1979 | Illy | 521/95 |
| 4,636,457 | A | 1/1987 | Valbusa et al. | 430/267 |
| 4,921,965 | A | 5/1990 | Rothgery et al. | 548/251 |
| 4,988,811 | A | 1/1991 | Valbusa et al. | 544/207 |
| 5,773,754 | A | 6/1998 | Yamato | 149/36 |
| 6,074,502 | A | 6/2000 | Burns et al. | 149/36 |
| 6,552,051 | B2 | 4/2003 | Bottaro et al. | 514/359 |
| 6,590,118 | B1 | 7/2003 | Kristiansen et al. | 558/416 |
| 7,237,801 | B2 | 7/2007 | Quioc et al. | 280/736 |
| 7,399,841 | B1 * | 7/2008 | Koppes et al. | 534/556 |
| 7,692,024 | B2 | 4/2010 | Ganta et al. | 548/250 |
| 7,847,102 | B2 | 12/2010 | Ganta et al. | 548/251 |
| 2003/0145923 | A1 | 8/2003 | Redecker et al. | 149/36 |

(Continued)

FOREIGN PATENT DOCUMENTS
WO  WO 2006/050442  5/2006

OTHER PUBLICATIONS

Condensed Tetrazolo-1,3,5-Triazines, Federov.*

(Continued)

*Primary Examiner* — Aileen Felton
(74) *Attorney, Agent, or Firm* — L. C. Begin & Associates, PLLC.

(57) ABSTRACT

A novel compound, used for example, as a gas generating fuel, is defined as a compound having the structural formula of

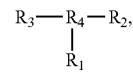

wherein: R4 is a triazine ring; R1 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; R2 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; R3 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles.

11 Claims, 1 Drawing Sheet

U.S. PATENT DOCUMENTS

| | | | | |
|---|---|---|---|---|
| 2004/0053908 | A1 | 3/2004 | Funahashi et al. | 514/183 |
| 2004/0226639 | A1* | 11/2004 | Redecker et al. | 149/45 |
| 2005/0263224 | A1 | 12/2005 | Wu et al. | 149/46 |
| 2006/0005734 | A1 | 1/2006 | McCormick | 102/530 |
| 2006/0016529 | A1 | 1/2006 | Barnes et al. | 149/45 |
| 2007/0102076 | A1 | 5/2007 | Redecker et al. | 149/36 |
| 2008/0110536 | A1 | 5/2008 | Ganta et al. | 149/45 |
| 2008/0154044 | A1 | 6/2008 | Ganta et al. | 548/251 |
| 2008/0169051 | A1 | 7/2008 | Ganta et al. | |

OTHER PUBLICATIONS

Office Action U.S. Appl. No. 11/800,923, filed May 7, 2007; Dated for Apr. 15, 2009.
Office Action U.S. Appl. No. 11/800,172, filed May 4, 2007; Dated for Apr. 8, 2009.
Office Action U.S. Appl. No. 11/800,923, filed May 7, 2007, Dated Apr. 1, 2010.
PCT Written Opinion, PCT/US07/11051, dated Nov. 27, 2007.
PCT Written Opinion, PCT/US07/11108, dated Apr. 15, 2008.
PCT Written Opinion, PCT/US07/11096, dated Apr. 30, 2008.
PCT Written Opinion, PCT/US07/11109 dated Apr. 24, 2008.
PCT Written Opinion, PCT/US07/11107, dated Jun. 3, 2008.
PCT Written Opinion, PCT/US07/21142, dated Aug. 1, 2008.
Fleming et al., Reactions of bis(tetrazole)phenylenes, Surprising formation of vinyl compounds from alkyl halides. Tetrahedron. May 2005, vol. 61(29), pp. 7002-7011, especially p. 7003.
Demko et al. Preparation of 5-Substituted1H-Tetrazoles from Nitriles in Water. J. Org. Chem. Jun. 2001, vol. 66(24), pp. 7945-7950, especially p. 7946.
Office Action U.S. Appl. No. 11/800,923, filed May 7, 2007; Dated for Sep. 15, 2008.
Office Action U.S. Appl. No. 11/800,922, filed May 7, 2007, Mailed Jan. 14, 2011.
Office Action U.S. Appl. No. 12/916,742, filed Nov. 1, 2010, Mailed Mar. 2, 2011.

* cited by examiner

GAS GENERANT COMPOSITIONS

CROSS-REFERENCE TO RELATED APPLICATIONS

This application claims the benefit of U.S. Provisional Application Ser. No. 60/848,684 filed on Sep. 30, 2006.

TECHNICAL FIELD

The present invention relates generally to gas generating systems, and to gas generant compositions employed in gas generator devices for automotive restraint systems, for example.

BACKGROUND OF THE INVENTION

The present invention relates to gas generant compositions that upon combustion produce a relatively small amount of solids and a relatively abundant amount of gas. It is an ongoing challenge to reduce the amount of solids and increase the amount of gas thereby decreasing the filtration requirements for an inflator. As a result, the filter may be either reduced in size or eliminated altogether thereby reducing the weight and/or size of the inflator.

An equally important challenge is to manufacture gas generants that exhibit relatively low sensitivity with regard to impact, friction, or electrostatic discharge stimuli.

Accordingly, it would be an improvement in the art to provide compositions that contain constituents that contain little or no metals and that contribute to a "smokeless" gas generant composition, or one that when combusted produces 90% or more of gas as a product.

To that end, the manufacture of fuels, oxidizers, and other constituents known for their use in gas generant compositions for example, and exhibiting the above advantages, is desirable.

SUMMARY OF THE INVENTION

The above-referenced concerns are resolved by the manufacture of gas generant fuels that contain relatively high amounts of nitrogen and carbon thereby contributing to gaseous products as opposed to solid products upon combustion of a gas generant containing the fuel. The fuels are described as triazine-based molecules containing one, two, and three tetrazole rings on a triazine system. The fuels are described as triazine-based molecules containing one, two, and three tetrazole rings on a triazine system. Stated another way, the fuels of the present invention are defined as having the structural formula of:

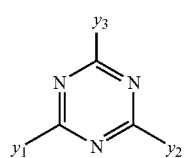

$Y_1$ is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; $Y_2$ is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; $Y_3$ is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; and at least one of $Y_1$, $Y_2$, or $Y_3$ is a tetrazolyl group.

Stated another way, the fuels of the present invention are defined as having the structural formula of:

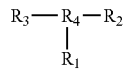

wherein R4 is a triazine ring; R1 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; R2 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; R3 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; and at least one of R1, R2, or R3 is a tetrazolyl group.

In one aspect of the present invention, tetrazolo-triazine molecules and their corresponding derivatives have high energy and provide high gas yield per mole of gas generant. The high energy is especially beneficial when employing oxidizers such as phase stabilized ammonium nitrate that require greater amounts of energy to sustain combustion.

In further accordance with the present invention, a gas generator and a vehicle occupant protection system incorporating the gas generant composition are also included.

DETAILED DESCRIPTION

Figure 1:
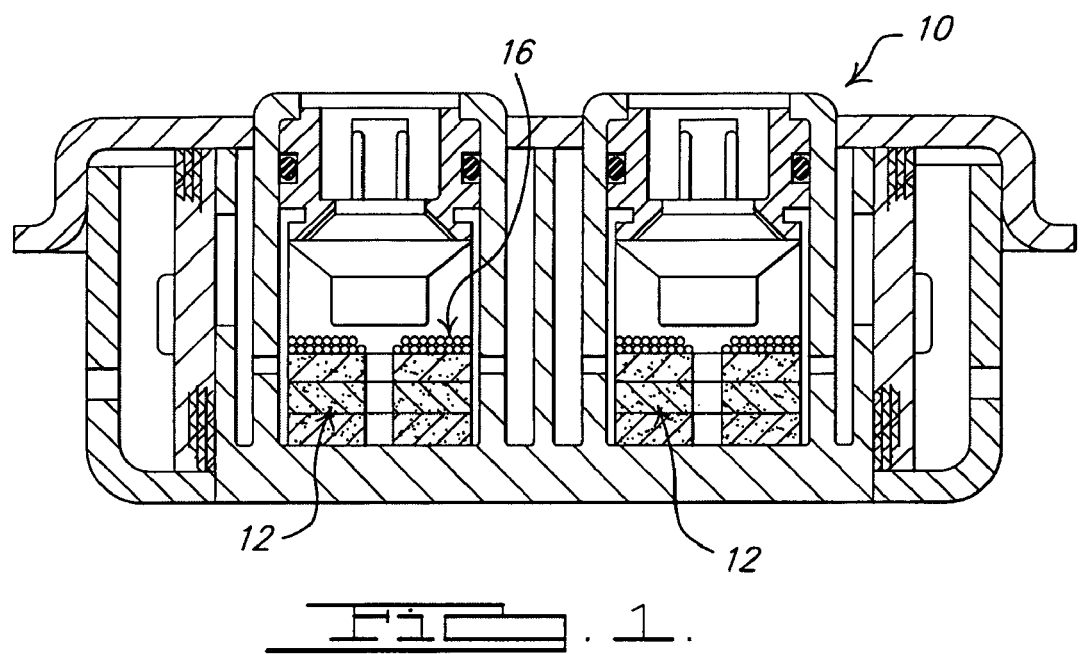
FIG. 1 is a cross-sectional side view showing the general structure of an inflator in accordance with the present invention.

The present invention includes gas generant compositions that in accordance with the present invention contain a first fuel selected from gas generant fuels that contain relatively high amounts of nitrogen and carbon thereby contributing to gaseous products as opposed to solid products upon combustion of a gas generant containing the fuel. The fuels are described as triazine-based molecules containing one, two, and three tetrazole rings on a triazine system. The molecules are believed to be novel and may also have other uses including rocket technology or defense-related applications given the high energy inherent in these fuels.

The following examples illustrate, but do not limit, various fuels as gas generant constituents, and the method of making the same.

EXAMPLE 1

2,4,6-tris(1-tetrazolyl)-1,3,5-Triazine

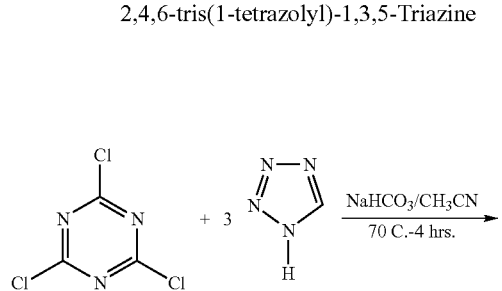

Experimental Procedure for the Synthesis of 2,4,6-tris(1-tetrazolyl)-1,3,5-Triazine A solution of 1H-Tetrazole (1.3 g, 18.5714 mmol) in acetonitrile (at about 3 wt % 1H-Tetrazole, from Aldrich) was prepared. NaHCO$_3$ (1.607 g, 19.1285 mmol) was added at about 0° C., and the mixture was stirred at room temperature for about 30 minutes. The reaction mixture was then cooled and brought to about 0° C. Cyanuric chloride (1.1415 g, 6.1904 mmol) was added to the mixture, and the mixture was stirred at room temperature for about 30 min and then warmed to and maintained at about 70° C. for 4 hrs. After 4 hrs, the reaction was brought to room temperature and poured into 200 ml of water within a flask. The mixture was stirred vigorously for about 30 minutes. A white solid was filtered from the solution and air dried to yield 2.2 g of pure material.

The formation of 2,4,6-tris(1-tetrazolyl)-1,3,5-Triazine was confirmed by IR spectroscopy; the absorption peaks at 1444, 1473 cm−1 correspond to triazine ring stretching; and the peak at 1587, 3110 cm−1 represents and confirms the tetrazole moiety in the compound.

OB=−75.74.

This material is detonable on heating and friction sensitive. As such, as with all other similarly sensitive types of compounds, these and other highly energetic compounds of the present invention should be processed and handled in accordance with enhanced safety considerations as recognized by those of ordinary skill in the art.

Theoretically if the Prop OB=−0.52, then the ratio of fuel/oxidizer is 23/77; the resultant gas yield is about 96.4% relative to total combustion products, and produces 4.04 moles of gas per 100 gm of propellant.

EXAMPLE 2

2,4-Bi(tetrazolo)-6-Chloro-1,3,5-Triazine

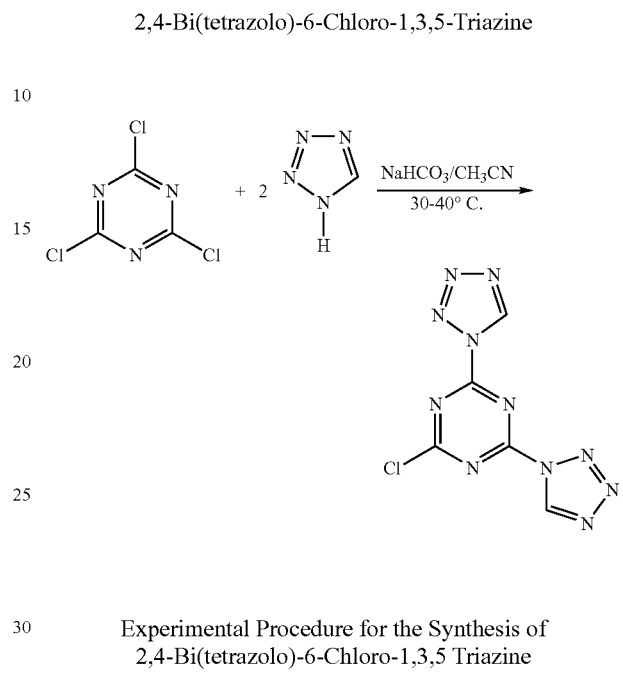

Experimental Procedure for the Synthesis of 2,4-Bi(tetrazolo)-6-Chloro-1,3,5 Triazine A solution of 1H-Tetrazole (1.3 g, 18.5714 mmol) in acetonitrile (at about 3 wt % 1H-Tetrazole, from Aldrich) was prepared. NaHCO$_3$ (1.607 g, 19.1285 mmol) was added at about 0° C., and the mixture was stirred at room temperature for about 30 minutes. The reaction mixture was then cooled and brought to about 0° C. Cyanuric chloride (1.6952 g, 9.1928 mmol) was added to the mixture, and the mixture was stirred at room temperature for about 30 min and then warmed to and maintained at about 30-40° C. for 2 hrs. After 2 hrs, the reaction was brought to room temperature and poured into 200 ml of water within a flask. The mixture was stirred vigorously for about 30 minutes. A white solid was filtered from the solution and air dried to yield 2.2 g of pure material.

The formation of 2,4-Bi(tetrazolo)-6-Chloro-1,3,5 Triazine was confirmed by IR spectroscopy; the absorption peaks at 1455, 1475 cm−1 correspond to triazine ring stretching and 850 cm−1 for ring chlorine; the peaks at 1587, 3110 cm−1 represent and confirm the tetrazole moiety in the compound.

Note: This material is friction sensitive.

EXAMPLE 3

4-tetrazolyl-2,6-dichloro-Triazine

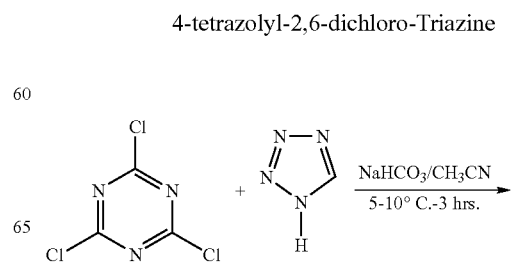

-continued

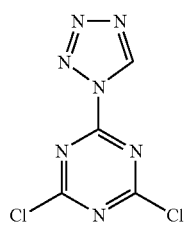

Experimental Procedure for the Synthesis of
4-tetrazolyl-2,6-dichloro-Triazine

A solution of 1H-Tetrazole (1.3 g, 18.5714 mmol) in acetonitrile (at about 3 wt % 1H-Tetrazole, from Aldrich) was prepared. $NaHCO_3$ (1.607 g, 19.1285 mmol) was added at about 0° C., and the mixture was stirred at room temperature for about 30 minutes. The reaction mixture was then cooled and brought to about 0° C. Cyanuric chloride (3.3905 g, 18.3856 mmol) was added to the mixture, and the mixture was stirred at room temperature for about 30 min and then warmed to and maintained at about 0-10° C. for 3 hrs. After 3 hrs, the reaction was brought to room temperature and poured into 200 ml of water within a flask. The mixture was stirred vigorously for about 30 minutes. The excess sodium bicarbonate impurities completely dissolved in water; a white solid was filtered from the solution and air dried to yield pure material.

The formation of 4-tetrazolyl-2,6-dichloro-Triazine was confirmed by IR spectroscopy; the absorption peaks at 1455, 1475 cm−1 correspond to triazine ring stretching and 850 cm−1 for ring chlorine; the peaks at 1587, 3110 cm−1 represent and confirm the tetrazole moiety in the compound.

Note: This material is friction sensitive

EXAMPLE 4

2,4-Di(methoxy)-6-tetrazolo-1,3,5-Triazine

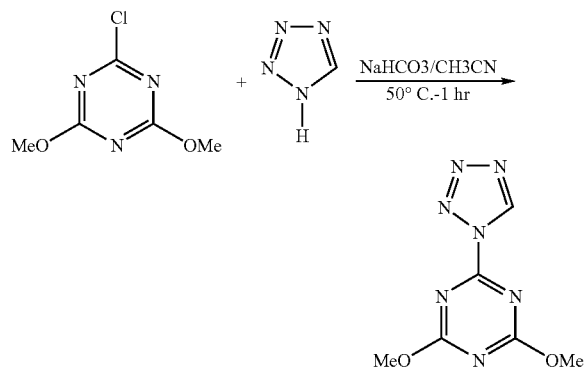

Experimental Procedure for the Synthesis of
2,6-Di(methoxy)-4-tetrazolo-1,3,5-Triazine A solution of 1H-Tetrazole (0.511 g, 5.7524 mmol) in acetonitrile (at about 3 wt % 1H-Tetrazole, from Aldrich) was prepared. $NaHCO_3$ (0.483 g, 5.7524 mmol) was added at about 0° C., and the mixture was stirred at room temperature for about 30 minutes. The reaction mixture was then cooled and brought to about 0° C. Chloro-4,6-dimethoxy triazine (1.000 g, 5.6954 mmol) was added to the mixture, and the mixture was stirred at 55° C. for about 3-4 hours. After 4 hrs, the reaction mixture poured into 100 ml of water and then extracted with 100 ml of Ethyl acetate. The solvent was dried over MgSO4 and evaporated under reduced pressure to yield white powder.

The formation of 2,4-Di(methoxy)-6-tetrazolo-1,3,5-Triazine was confirmed by IR spectroscopy; the absorption peaks at 1465, 1479 cm−1 correspond to triazine ring stretching, 2962 cm−1 for methoxyl group; the peaks at 1587, 1610 and 3110 cm−1 represent and confirm the tetrazole moiety in the compound.

DSC: broad exotherm at 162° C., and forms aerosol on heating.

Note: This material is friction sensitive.

EXAMPLE 5

2-methoxy-4,6-Bi(tetrazolo)-1,3,5-Triazine

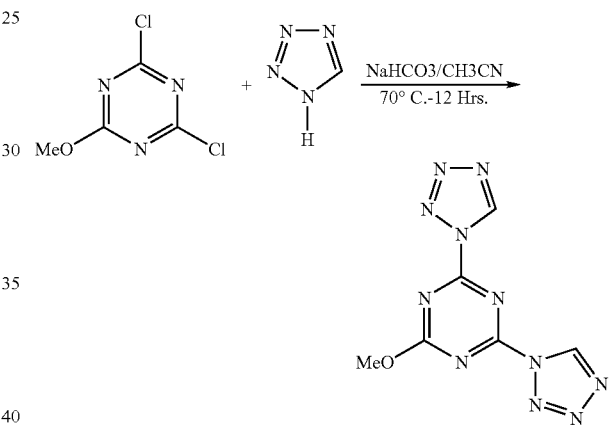

Experimental Procedure for the Synthesis of
2-methoxy-4,6-Bi(tetrazolo)-1,3,5-Triazine A solution of 1H-Tetrazole (0.511 g, 5.7524 mmol) in acetonitrile (at about 3 wt % 1H-Tetrazole, from Aldrich) was prepared. $NaHCO_3$ (0.483 g, 5.7524 mmol) was added at about 0° C., and the mixture was stirred at room temperature for about 30 minutes. The reaction mixture was then cooled and brought to about 0° C. 2,4-dichloro-6-methoxy triazine (1.000 g, 5.6954 mmol) at 0° C. was added to the mixture, and the mixture was stirred at about 70° C. overnight. After 12 hrs, the reaction mixture poured into 100 ml of ethyl acetate. The solvent was dried over $MgSO_4$ and evaporated under reduced pressure to yield white powder.

The formation of 2-methoxy-4,6-Bi(tetrazolo)-1,3,5-Triazine was confirmed by IR spectroscopy; the absorption peaks at 1453, 1477 cm−1 correspond to triazine ring stretching, 3133 cm−1 for methoxyl group; the peaks at 1558, 1604 represent and confirm the tetrazole moiety in the compound.

DSC: Sharp exotherm at 145° C.

This material with PSAN burns well, but turns into slight brown color on aging with PSAN @ 107 C.

Note: This material is friction sensitive

EXAMPLE 6

2,4-Di(methoxy)-2-tetrazolo-1,3,5-Triazine

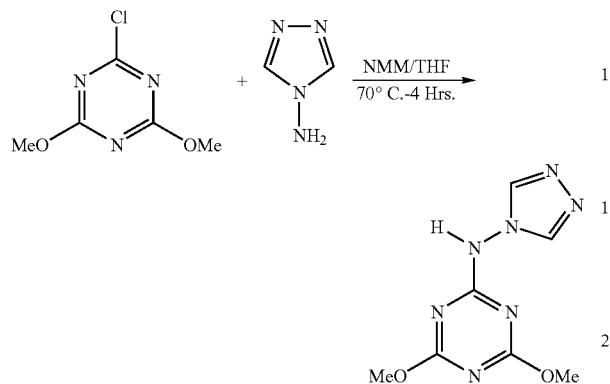

Experimental Procedure for the Synthesis of 2,4-dimethoxy-6-(amino triazolo)-1,3,5-Triazine A solution of 2-chloro-4,6-dimethoxy triazine (1.000 g, 5.6954 mmol) in tetrahydrofuran (from Aldrich) was prepared. N-methyl morpholine (0.6336 g, 6.2649 mmol) was added at room temperature, and the mixture was stirred at room temperature for about 30 minutes. 4-amino triazole was added to the mixture and the mixture was slowly warmed to The reaction mixture was then cooled and brought to about 70° C. for 4 hours. After 4 hrs, the slurry was poured into 40 ml of water, and a white colored compound was separated therefrom.

The formation of 2,4-Di(methoxy)-2-tetrazolo-1,3,5-Triazine was confirmed by IR spectroscopy; the absorption peaks at 1639, 1525 cm−1 correspond to triazole ring stretching, 3386 cm−1 for secondary amine stretching; the peaks at 1593, 1548 cm−1 represent and confirm the triazine moiety in the compound.

DSC: Sharp exotherm at 160° C.

EXAMPLE 7

2,4-Di(methoxy),5-acetamidotetrazolo-1,3,5-Triazine

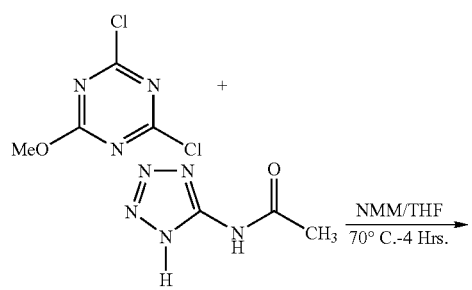

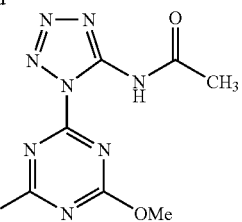

Experimental Procedure for the Synthesis 2,4-Di(methoxy),5-acetamidotetrazolo-1,3,5-Triazine A solution of 2,4-dichloro-6-methoxy triazine (1.000 g, 5.6954 mmol) in tetrahydrofuran (from Aldrich) was prepared. N-methyl morpholine (0.6336 g, 6.2649 mmol) was added at room temperature, and the mixture was stirred at room temperature for about 30 minutes. 5-acetamido tetrazole was then added to the mixture and the mixture was slowly warmed to 70° C. for 4 hours. After 4 hrs, the slurry was poured into 40 ml of water, and a white colored compound was separated therefrom. The material was air dried to yield solid powder.

The formation of 2,4-Di(methoxy),5-acetamidotetrazolo-1,3,5-Triazine was confirmed by IR spectroscopy; the absorption peaks at 1693 for acetamide, 1610, 1550 cm−1 for tetrazole ring stretching, 3010 cm−1 for amide N—H, and the peak at 1482, 1190 cm−1 represents and confirms the triazine moiety in the compound.

DSC: Very sharp exotherm at 180° C. and it ignites well and burns very well.

This material on aging loses its mass (about 4%). This fuel at about 17 wt % when mixed with phase stabilized ammonium nitrate (stabilized with potassium nitrate in a known manner) at about 83 wt % burns extremely well, but loses mass about 4.8% after 400 Hrs @ 107 C.

OB: −108.2

EXAMPLE 8

2,4-Di(methoxy),6-(5-aminotetrazolo)-1,3,5-Triazine

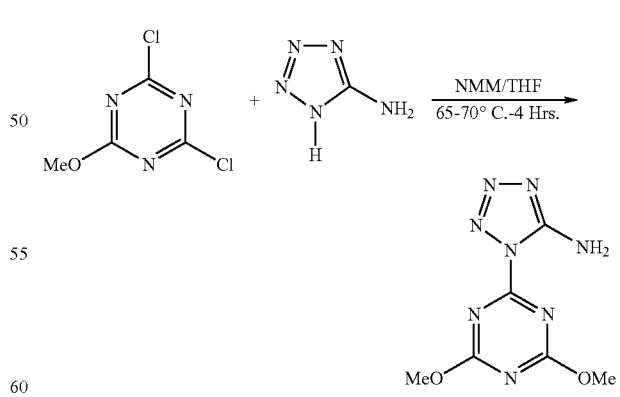

Experimental Procedure for the Synthesis 2,4-Di(methoxy),6-(5-aminotetrazolo)-1,3,5-Triazine A solution of 2,4-dichloro-6-methoxy triazine (1.000 g, 5.6954 mmol) in tetrahydrofuran (from Aldrich) was prepared. N-methyl morpholine (0.6336 g, 6.2649 mmol) was added at room temperature, and the mixture was stirred at room temperature for about 30 minutes as a white precipitate was observed. Potassium 5-amino tetrazole was then added to the mixture and the mixture was slowly warmed to 65-70° C. for 4 hours. After 4 hours, the slurry was poured into 40 ml of water, and a white colored compound was separated therefrom. The material was air dried to yield solid powder.

The formation of 2,4-Di(methoxy),6-(5-aminotetrazolo)-1,3,5-Triazine was confirmed by IR spectroscopy; the absorption peaks at 3318, 3404 cm−1 for primary amine, 1638, 1593 cm−1 for tetrazole ring stretching, and the peaks at 1554, 1386, 950 cm−1 represent and confirm the triazine moiety in the compound.

DSC: Very sharp and symmetric exotherm at 166° C.
OB: −99.91

EXAMPLES 9 AND 10

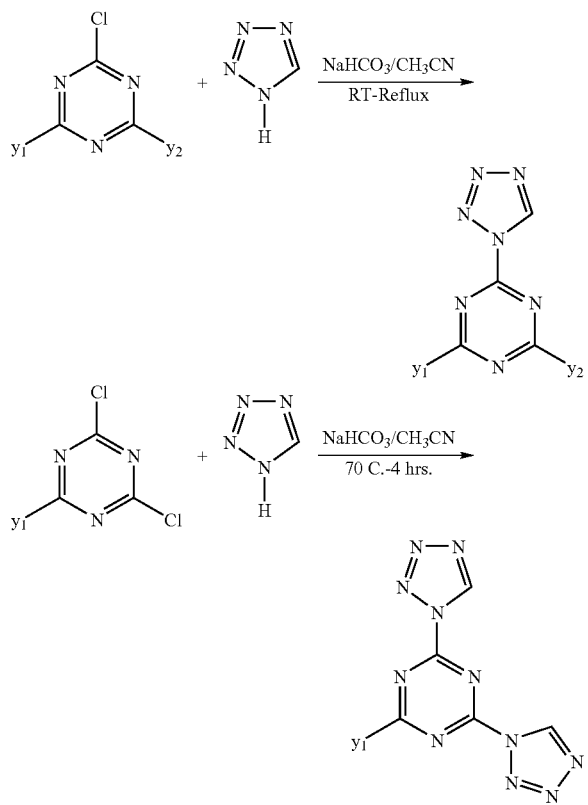

Examples 9 and 10 illustrate how known triazine-based compounds substituted at the Y1 and/or Y2 positions as shown and as known in the art may result in a number of fuels in accordance with the present invention. Y1 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; and Y2 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles. Syntheses and/or suppliers for the various starting reagents are known in the art, and include companies such as Aldrich, Fisher Chemical, and reactions as delineated herein.

Other gas generant constituents may be combined with the primary fuels described herein and may be combined to form gas generant compositions as known in the art. The constituents described below exemplify but do not limit the gas generant constituents that may be combined with the novel fuels described herein. The first fuel as formed in accordance with the present invention and as exemplified in the examples given above, is provided at about 0.1 to 80 weight percent of the total gas generant composition, and more preferably at about 5-50 wt % of the gas generant composition.

A first oxidizer selected from the group including nonmetal and metal nitrate salts such as ammonium nitrate, phase-stabilized ammonium nitrate, potassium nitrate, strontium nitrate; nitrite salts such as potassium nitrite; chlorate salts such as potassium chlorate; metal and nonmetal perchlorate salts such as potassium or ammonium perchlorate; oxides such as iron oxide and copper oxide; basic nitrate salts such as basic copper nitrate and basic iron nitrate; and mixtures thereof. The first oxidizer is generally provided at about 5-95 wt % of the gas generant composition, and more preferably at about 10-70 wt %.

An optional secondary oxidizer may also be provided and selected from the oxidizers described above, and when included is generally provided at about 0.1-50 wt %, and more preferably at about 0.1-30 wt %. The total oxidizer component, that is the combined weight percent of all oxidizers, will nevertheless only range from 0.1 to 80 wt %.

An optional secondary fuel is selected from the group containing derivatives of bis-(1(2)H-tetrazol-5-yl)-amine, including mono-ammonium salt of bis-(1(2)H-tetrazol-5-yl)-amine (BTA-1NH3), its anhydrous acid, its acid monohydrate, metal salts thereof including the potassium, sodium, strontium, copper, boron, zinc salts of BTA-1NH3; complexes thereof; azoles such as 5-aminotetrazole; metal salts of azoles such as potassium 5-aminotetrazole; nonmetal salts of azoles such as mono- or di-ammonium salt of 5,5'-bis-1H-tetrazole; nitrate salts of azoles such as 5-aminotetrazole nitrate; nitramine derivatives of azoles such as 5-nitraminotetrazole; metal salts of nitramine derivatives of azoles such as di-potassium 5-nitraminotetrazole; nonmetal salts of nitramine derivatives of azoles such as mono- or di-ammonium 5-nitraminotetrazole and; guanidines such as dicyandiamide; salts of guanidines such as guanidine nitrate; nitro derivatives guanidines such as nitroguanidine; azoamides such as azodicarbonamide; nitrate salts of azoamides such as azodicarbonamidine dinitrate; and mixtures thereof, and when included is generally provided at about 0.1-49.9 wt %, more preferably 0.1-30 wt %. The total fuel component, that is the combined amount of all of the fuels of the composition, will nevertheless only range from 0.1-50 wt %, and more preferably about 0.1-30 wt %.

Optional additives are selected from the group including fumed metal oxides such as fumed silica or fumed alumina, silicon compounds including elemental silicon, silicon dioxide, and fused silica; silicones such as polydimethylsiloxane; silicates such as potassium silicates; natural minerals such as talc, mica, and clay; lubricants such as graphite powder or fibers, magnesium stearate, boron nitride, molybdenum sulfide; and mixtures thereof, and when included is generally provided at about 0.1-10%, and more preferably at about 0.1-5%.

An optional binder is selected from the group of cellulose derivatives such as cellulose acetate, cellulose acetate butyrate, carboxymethylcellulose, salts of carboxymethylcellulose, carboxymethylcellulose acetate butyrate; silicone; polyalkene carbonates such as polypropylene carbonate and polyethylene carbonate; and mixtures thereof, and when included is generally provided at about 0.1-10%, and more preferably at about 0.1-5%.

All percentages for the constituents described herein are presented as weight percents of the total gas generant weight.

It has been determined that the addition of small amounts of fumed metal oxides, such as fumed silica (M-5 Grade provided by the Cabot Corporation), to these formulations provides a gas generant which exhibits all of the favorable properties listed above, and, more importantly, exhibits stable ballistic performance when subjected to thermal cycling or thermal shock conditioning.

Dry mixes of formulations containing these materials can be made as known in the art. The raw materials for example may be ground together for 15 minutes in a Sweco vibratory mill. The dry material may then be tableted and loaded into inflators for use thereof.

As shown in FIG. 1, an exemplary inflator incorporates a dual chamber design to tailor the force of deployment an associated airbag. In general, an inflator containing a primary gas generant 12 formed as described herein, may be manufactured as known in the art. U.S. Pat. Nos. 6,422,601, 6,805,377, 6,659,500, 6,749,219, and 6,752,421 exemplify typical airbag inflator designs and are each incorporated herein by reference in their entirety.

Figure 2:
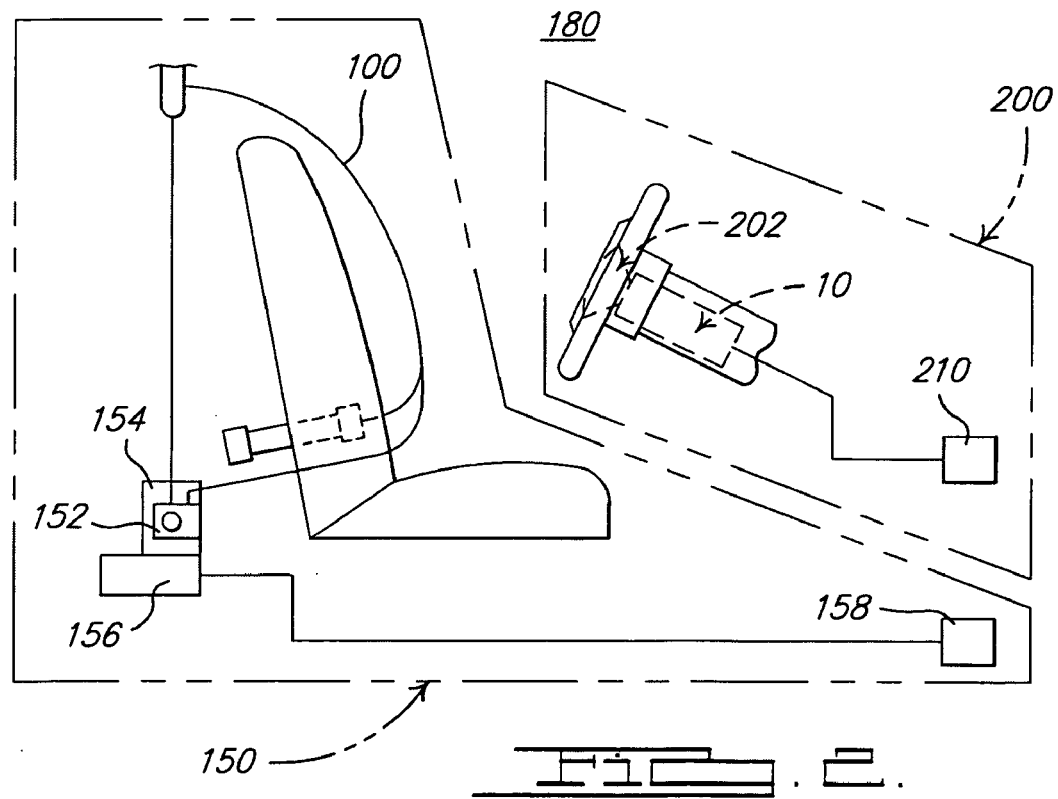
FIG. 2 is a schematic representation of an exemplary vehicle occupant restraint system containing a gas generant composition in accordance with the present invention.

Referring now to FIG. 2, the exemplary inflator 10 described above may also be incorporated into a gas generating system or airbag system 200. Airbag system 200 includes at least one airbag 202 and an inflator 10 containing a gas generant composition 12 in accordance with the present invention, coupled to airbag 202 so as to enable fluid communication with an interior of the airbag. Airbag system 200 may also include (or be in communication with) a crash event sensor 210. Crash event sensor 210 includes a known crash sensor algorithm that signals actuation of airbag system 200 via, for example, activation of airbag inflator 10 in the event of a collision.

Referring again to FIG. 2, airbag system 200 may also be incorporated into a broader, more comprehensive vehicle occupant restraint system 180 including additional elements such as a safety belt assembly 150. FIG. 2 shows a schematic diagram of one exemplary embodiment of such a restraint system. Safety belt assembly 150 includes a safety belt housing 152 and a safety belt 100 extending from housing 152. A safety belt retractor mechanism 154 (for example, a spring-loaded mechanism) may be coupled to an end portion of the belt. In addition, a safety belt pretensioner 156 containing propellant 12 and autoignition 14 may be coupled to belt retractor mechanism 154 to actuate the retractor mechanism in the event of a collision. Typical seat belt retractor mechanisms which may be used in conjunction with the safety belt embodiments of the present invention are described in U.S. Pat. Nos. 5,743,480, 5,553,803, 5,667,161, 5,451,008, 4,558,832 and 4,597,546, incorporated herein by reference. Illustrative examples of typical pretensioners with which the safety belt embodiments of the present invention may be combined are described in U.S. Pat. Nos. 6,505,790 and 6,419,177, incorporated herein by reference.

Safety belt assembly 150 may also include (or be in communication with) a crash event sensor 158 (for example, an inertia sensor or an accelerometer) including a known crash sensor algorithm that signals actuation of belt pretensioner 156 via, for example, activation of a pyrotechnic igniter (not shown) incorporated into the pretensioner. U.S. Pat. Nos. 6,505,790 and 6,419,177, previously incorporated herein by reference, provide illustrative examples of pretensioners actuated in such a manner.

It should be appreciated that safety belt assembly 150, airbag system 200, and more broadly, vehicle occupant protection system 180 exemplify but do not limit gas generating systems contemplated in accordance with the present invention. Further, the compositions described above do not limit the present invention.

It should be understood that the preceding is merely a detailed description of various embodiments of this invention and that numerous changes to the disclosed embodiments can be made in accordance with the disclosure herein without departing from the scope of the invention. The preceding description, therefore, is not meant to limit the scope of the invention. Rather, the scope of the invention is to be determined by equivalents of the gas generant constituents described incorporating the novel fuels described above.

What is claimed is:

1. A compound defined as having the structural formula of

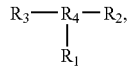

wherein: R4 is a triazine ring; R1 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; R2 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; R3 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; and at least one of R1, R2, or R3 is a tetrazolyl group.

2. The compound of claim 1 wherein R1, R2, and R3 are tetrazolyl groups.

3. The compound of claim 1 wherein R1 and R2 are tetrazolyl groups, and R3 is selected from the group consisting of CH3, OCH3, —CN, —C2H, NCO, —NHNH2, NO, NO2, OH, Cl, —NHCONH2, —OCOR, NHNO2, substituted tetrazoles, and substituted triazoles.

4. The compound of claim 1 wherein R1 is a tetrazolyl group, and R2 and R3 are each selected from the group consisting of CH3, OCH3, —CN, —C2H, NCO, —NHNH2, NO, NO2, OH, Cl, —NHCONH2, —OCOR, NHNO2, substituted tetrazoles, and substituted triazoles.

5. A composition comprising:
a first fuel defined as having the structural formula of

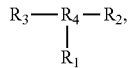

wherein: R4 is a triazine ring; R1 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; R2 is selected from the group consisting of a tetrazolyl group, CH3, OCH3, —CN, —C2H, NCO, —NHNH2, NO, NO2, OH, Cl, —NHCONH2, —OCOR, NHNO2, substituted tetrazoles, and substituted triazoles; R3 is selected from the group consisting of a tetrazolyl group, CH3, OCH3, —CN, —C2H, NCO, —NHNH2, NO, NO2, OH, Cl, —NH- CONH2, —OCOR, NHNO2, substituted tetrazoles, and substituted triazoles; and at least one of R1, R2, or R3 is a tetrazolyl group, said fuel provided at about 5-95 weight percent;

an oxidizer selected from basic metal nitrates, and, metal and nonmetal nitrates, chlorates, perchlorates, nitrites, oxides, and peroxides, said oxidizer provided at about 5-95 weight percent.

6. The composition of claim 4 further comprising:

a second fuel selected from carboxylic acids; amino acids; tetrazoles; triazoles; guanidines; azoamides; metal and nonmetal salts thereof; and mixtures thereof, said second fuel provided at about 0.1-30 percent.

7. A gas generating system containing the compound of claim 1.

8. A vehicle occupant protection system containing the compound 1.

9. A gas generating system containing the composition of claim 5.

10. A vehicle occupant protection system containing the composition of claim 5.

11. A composition containing the compound of claim 1.

* * * * *